United States Patent
Hicks et al.

(10) Patent No.: US 8,969,096 B2
(45) Date of Patent: Mar. 3, 2015

(54) AUTOMOTIVE FOGGING ANALYSES BY XENON UV EXPOSURE

(75) Inventors: David Lee Hicks, Fowlerville, MI (US); Mark Timothy Bacchus, Ypsilanti, MI (US)

(73) Assignee: Toyota Motor Engineering & Manufacturing North America, Inc., Erlanger, KY (US)

(*) Notice: Subject to any disclaimer, the term of this patent is extended or adjusted under 35 U.S.C. 154(b) by 610 days.

(21) Appl. No.: 13/223,967

(22) Filed: Sep. 1, 2011

(65) Prior Publication Data
US 2013/0059397 A1  Mar. 7, 2013

(51) Int. Cl.
G01N 21/75 (2006.01)
G01N 21/57 (2006.01)
G01N 21/3504 (2014.01)
G01N 21/35 (2014.01)

(52) U.S. Cl.
CPC ............ *G01N 21/57* (2013.01); *G01N 21/3504* (2013.01); *G01N 2021/3595* (2013.01)
USPC ......................................................... 436/164

(58) Field of Classification Search
CPC ..................................................... G01N 21/75
USPC ......................................................... 436/164
See application file for complete search history.

(56) References Cited

U.S. PATENT DOCUMENTS

| | | | |
|---|---|---|---|
| 4,003,257 A | 1/1977 | Fletcher et al. | |
| 5,387,263 A | 2/1995 | Marlowe et al. | |
| 5,773,833 A | 6/1998 | Hsi | |
| 6,053,059 A * | 4/2000 | Muranaka et al. | 73/863.12 |
| 6,594,016 B1 | 7/2003 | Te Lintel Hekkert et al. | |
| 2003/0194506 A1 | 10/2003 | Drzal et al. | |
| 2005/0044991 A1* | 3/2005 | Guo et al. | 75/721 |
| 2008/0182931 A1 | 7/2008 | Manning et al. | |

FOREIGN PATENT DOCUMENTS

GB    2029015 A *  3/1980  ............. G01N 33/02

OTHER PUBLICATIONS

Sebedio et al. (JAOCS, vol. 64, No. 9 (Sep. 1987)).*
Scott Pratt; Understanding a Fog Testing System; Thermo Fisher Scientific, Newington, NH, USA; Application Note: ANTCFOGTEST0311.
Thermo Haake GmbH; Temperature Control Unit for the Fogging Test acc. to DIN 75201 and ISO 6452/2000.

* cited by examiner

*Primary Examiner* — Christopher A. Hixson
*Assistant Examiner* — Emily Berkeley
(74) *Attorney, Agent, or Firm* — Gifford, Krass, Sprinkle, Anderson & Citkowski, P.C.

(57) ABSTRACT

Processes and apparatuses are provided for the liberation of one or more volatile organic compounds from a test sample. The processes include exposing a sample to light of a wavelength less than 400 nm, subjecting the sample to heat, and collecting one or more volatile organic compounds produced from the sample. The volatile organic compounds are detected by any of various methods, and are optionally identified by methods such as FTIR. The processes and apparatus provide for improved detection of relevant volatile organic compounds that are otherwise undetectable by traditional processes.

11 Claims, 4 Drawing Sheets

AUTOMOTIVE FOGGING ANALYSES BY XENON UV EXPOSURE

FIELD OF THE INVENTION

The invention relates to apparatuses and processes for the detection and identification of one or more volatiles that may produce fogging on a surface. More specifically, processes are provided for identification of one or more volatile organic compounds emitted from one or more materials used in automotive interiors.

BACKGROUND OF THE INVENTION

Automobile manufacture increasingly requires assembly of several material types placed in close proximity. It is not atypical for natural products such as leathers to be used in close proximity to synthetic materials that are included in padding, stitching, carpet or surface covers, among other locations in a vehicle interior.

The materials used in an automobile interior are exposed to widely varying environmental conditions such as high heat or extreme cold that may alter their appearance or compromise their physical integrity. For example, a vehicle placed in direct sunlight can experience internal cabin temperatures in excess of 110° C. These temperatures may have several detrimental consequences including the formation of volatiles from materials that may lead to fogging on interior surfaces, window glass, or other areas.

The increasing number of material types and chemistry, as well as the environmental conditions these materials may be exposed to in use or manufacture, necessitates testing procedures and systems to determine if the material is susceptible to formation of unwanted volatiles that may harm other materials or a user. Thus, there is a need for improved processes of detecting or identifying volatile formation from materials.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

A process for improved, specific, and relevant detection of volatiles produced from samples is provided. A process includes exposing a first sample to light with a wavelength less than 400 nanometers for a first time in a test chamber, and subjecting the first sample to a temperature. The process further includes detecting the presence or absence of one or more volatiles from the sample, reaction products thereof, or degradation products thereof, produced during the exposing and subjecting. The process optionally further includes collecting volatiles on a substrate, on a wall or other portion of a test chamber, or from a sample of the atmosphere within the test chamber.

The light to which a sample is exposed optionally includes UVA light that has a wavelength between or including the entire range of 315 nm to 400 nm.

A sample is subjected to heat. This temperature is optionally any value from 35° C. to 85° C. A temperature is optionally in excess of 25° C.

A sample is optionally exposed to light and subjected to heat at the same time.

A process optionally includes one or more phases. A first phase optionally includes exposing a sample to an irradiation phase for the first time; incubating the sample for a rest time; and re-exposing the sample to light, and optionally heat, for a second time. The second time is optionally greater than the first time. A rest time is any desired time, optionally sufficient for a sample to cool to room temperature, optionally 30 seconds or more.

A process optionally includes placing a second sample in a test chamber. A second sample is optionally placed in a position so as to be exposed or subjected to the same environmental conditions as the first sample, or placed in a position so as to be exposed to a different set of environmental conditions. Optionally, a second sample is placed behind a support relative to the direction of a light source where the support transmits less than 1% of the light onto the second sample.

A process optionally includes detecting or identifying one or more volatiles, reaction products of one or more volatiles, or degradation products of one or more volatiles. In some embodiments, these volatiles, reaction products, or degradation products are detected by FTIR.

Also provided is an apparatus capable of use in performing an inventive process. An apparatus includes a test chamber having a vertical midline, a wall, and a floor area where at least a portion of the wall is capable of transmitting greater than 70% of light between 315 nm and 400 nm. An apparatus further includes a support having an outer shape and positioned within the test chamber, and a substrate movably or removably associated with the test chamber at a position above a midpoint of the test chamber. An apparatus further includes a light source.

A support is included fixedly or removably associated with the interior of a test chamber. A support is optionally positioned across the vertical midline of the test chamber. A support has a first side and a second side, where the first side is positioned to be exposed to light transmitted through the wall. The second side forms a light exclusion region that blocks exposure of a sample placed in the light exclusion region to the majority of light emitted by the light source. The support includes a face. A face optionally extends at an angle of 45 degrees to a floor area. A support is optionally positioned within the test chamber such that said first side forms a light exposure area whereby a first sample is removably positionable in contact with the first side so as to be exposed to light transmitted by said portion of the wall. A support optionally extends 50% or more over a floor area of a test chamber. A support further has an outer shape. The outer shape is optionally complementary to an inner shape of the test chamber.

A test chamber includes a wall, or portion of a wall, that is transparent to light emitted by the light source. A wall is optionally formed of quartz of optical quality or other glass. A wall is optionally formed of glass used in automotive fields.

An apparatus includes one or more light sources. A light source is optionally a xenon lamp.

BRIEF DESCRIPTION OF THE DRAWINGS

The drawings are presented as non-limiting, specific examples of embodiments of the invention. The numbering is conserved between the figures for illustrative purposes. It is appreciated that the figures are not to scale.

DETAILED DESCRIPTION OF EMBODIMENTS OF THE INVENTION

Figure 1:
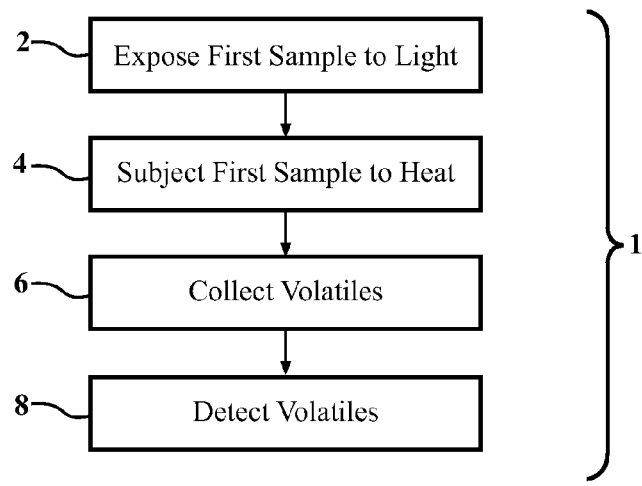
FIG. 1 represents one embodiment of a process according to the invention.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the process or apparatus is described as an order of individual steps or using specific materials, it is appreciated that described steps or materials may be interchangeable such that the description of the invention includes multiple parts or steps arranged in many ways as is readily appreciated by one of skill in the art.

Typical testing procedures for the presence of volatiles from materials exposed to environmental conditions that may form such volatiles are performed by exposing a sample to heat in a weathering chamber and determining whether a volatile is formed such as by collection of the volatiles on a surface in the form of a fog that reduces or alters the gloss or reflectivity of the collection surface. The art recognizes these processes as sufficient for testing and has developed international testing standards around these procedures.

The inclusion of multiple synthetic and/or natural materials in close proximity increases the likelihood of multiple volatile species forming simultaneously under similar environmental conditions. Depending on the chemistry, multiple volatiles may react to form reaction products that collect on surfaces creating fogging. While the prior testing procedures are capable of eliciting some volatiles from some materials, it has recently been discovered that some volatile reaction products are not produced under the traditional testing procedures. To address these concerns, new processes and systems for performing volatile production and detection are provided. The invention has utility for the creation and detection of one or more volatiles from a material created under desired environmental conditions.

Processes are provided for detecting one or more volatile compounds produced from one or more samples. A process includes exposing a first sample to a temperature at or in excess of a target temperature along with exposing the first sample to light of a predetermined wavelength, optionally collecting one or more volatiles, or volatile reaction products, from the sample on a substrate when one or more volatiles are created, and detecting the presence or absence of one or more volatile compounds on the substrate. The processes provided are capable of forming, collecting, and detecting the presence or absence of one or more volatile organic compounds, inorganic compounds, or combinations thereof, or reaction products thereof, optionally on a substrate, wall, or other region of a test chamber or combinations thereof. The specification will refer to volatiles as volatile organic compounds (VOC) for illustrative and exemplary purposes alone. The term "volatile organic compounds" and the acronym "VOC" are defined therein to incorporate organic or inorganic compounds that are volatilized from one or more materials, reaction products of one or more organic or inorganic, or combination organic/inorganic volatiles, degradation products of one or more volatiles or volatile reaction products, or combinations thereof.

In some embodiments, a process detects the presence or absence of one or more VOCs produced from a sample exposed to one or more environmental conditions. The number of VOCs detectable is not limited. Optionally, the number of volatiles detectable is 1, 2, 3, 4, 5, 6, 7, 8, 9, 10, or more, or any value or range between 1 and 100. The number of samples is limited only by the size of the apparatus used for a testing procedure. Optionally, a first sample, second sample, third sample, fourth sample, or additional sample are simultaneously or sequentially exposed or subjected to one or more environmental conditions. Optionally, a first sample and additional sample are exposed or subjected to the same or differing environmental conditions by type or extent.

An inventive process includes exposing or subjecting a sample to one or more environmental conditions. An "environmental condition" is a temperature, humidity, light intensity, light wavelength, atmosphere composition, or other known environmental parameter. Optionally, a sample is exposed to cold or to heat at or above a target temperature. Temperature is optionally constant or variable over the course of the subjecting process. A target temperature is optionally any temperature from −40° C. to 150° C., or any value or range therebetween. Optionally, a target temperature is from 25° C. to 110° C., 25° C. to 85° C., or 35° C. to 80° C. Optionally, a target temperature is from 35° C. to 75° C. In some embodiments, a target temperature is 60° C.

An environmental condition is optionally light intensity. Light intensity is optionally constant or variable over the course of an exposure process. Light intensity (irradiance) may vary depending on the wavelength range exposed to the sample and the type of light emission device chosen. In some embodiments, irradiance is measured at 340 nm as one standard method. One of ordinary skill in the art can readily determine total irradiance based on irradiance curve data for a spectral range from any light source or by direct measurement such as using a photodiode detector. Optionally, light intensity is at or above 0.25 W/m$^2$. Optionally, light intensity at 340 nm is from 0.1 to 100 W/m$^2$, or any value or range therebetween. In some embodiments, irradiance at 340 nm is 0.55 W/m$^2$. In some embodiments, the irradiance of UV light is from 50 to 200 W/m$^2$ encompassing total irradiance between 300 nm and 400 nm. Optionally, the total light irradiance is less than or equal to two sun levels at the earth's surface at zero degrees latitude.

An environmental condition is optionally exposure to light of a particular wavelength or a range of wavelengths. The wavelength(s) of light is optionally constant over an exposure time or is variable. Optionally, a sample is exposed to light that is similar to sunlight such as that emitted from a xenon lamp, a sulfur plasma lamp, or other source of "white" or other light. VITALUX lamps deliver radiation similar to that of the sun in the ultraviolet and infrared wavelengths. Their short wave spectrum corresponds to global radiation from 280 to 400 nm. Optionally, a sample is exposed to ultraviolet light in the absence of other light wavelengths. A wavelength range that a sample is exposed to is optionally between 200 to 750 nm or any value or range therebetween. A wavelength range is optionally from 315 nm to 750 nm, 315 nm to 400 nm (UVA), 315-280 nm (UVB), from 200 to 400 nm, or combinations thereof. Optionally, a sample is exposed to light from approximately 180 nm to 1100 nm.

An environmental condition is optionally humidity. Humidity is optionally constant over an exposure time or is variable. Humidity is optionally between 40% and 99%, or any value or range therebetween. Optionally, humidity is from 50% to 95%. Optionally, humidity is higher for a first time than a second time. In some embodiments, humidity is lower when a sample is exposed to light than during a time when the sample is not exposed to light. As an illustrative example, a sample is exposed to light and 50% humidity for a first time, no light and 95% humidity for a second time, and light and 50% humidity for a third time. A sample is optionally exposed to lower humidity during an irradiation phase than during a rest phase.

A sample is optionally exposed to more than one environmental condition simultaneously or sequentially. Optionally, a sample is exposed to heat and light simultaneously for a first time (irradiation phase), heat only for a second time (rest phase), and heat and light for a third time (irradiation phase). Other combinations are envisioned as operable under the processes of the invention. An irradiation phase is optionally from 30 sec to 24 hours. A rest phase is optionally from 30 sec to 1 hour. An overall exposure or process time is optionally 24 hours or less.

A sample is exposed to one or more environmental conditions within a test chamber. A test chamber is any chamber capable of housing a sample and exposing or subjecting a sample to one or more controllable environmental conditions. A test chamber is optionally sealed or exposed to ambient conditions. An illustrative example of a test chamber is a quartz beaker. A test sample is optionally placed in a test chamber that includes at least a portion that is transparent to light of a desired wavelength.

In some embodiments, volatiles are collected on a substrate, a wall, or other portion of a test chamber, or combinations thereof. A substrate is any surface capable of collecting one or more VOCs. Optionally, a substrate is a glass (quartz, borosilicate, or other) surface (curved or planar). Other materials are similarly operable illustratively including polymeric materials such as polystyrene, polyvinyl chloride, polyethylene, polypropylene, among others known in the art. A substrate is optionally a planar surface or curved, or of different shapes on differing portions of the substrate. In some embodiments, a substrate is coated with a reflective material such that the substrate is suitable for reflective or gloss-type detection processes. Illustrative examples of a coating include tin, aluminum, or other reflective material known in the art. A substrate is optionally transparent. A transparent substrate allows a coating to be applied on a side of the substrate that is not exposed to a VOC. A substrate is optionally integral with or forms a wall or surface of a test chamber or is a structure exposed directly or indirectly to the interior of a test chamber.

A process includes detecting the presence or absence of one or more VOCs collected on a substrate or other surface of a test chamber. One or more VOCs are optionally detected by one or more of Fourier-transform infrared spectroscopy (FTIR), gas chromatography, mass spectrometry, glossometry, gravitometry, flame ionization, photo ionization, liquid chromatography, and combinations thereof. Glossometry is illustratively performed using a gloss meter available from Rhopoint Instruments, East Sussex, UK. Optionally, one or more VOCs are detected by FTIR. Methods of FTIR analyses are illustrated in Nishikida, K, et al., in Selected Applications of Modern FT-IR Techniques, Kodansha, Tokyo, Japan 1995. Techniques of GC-MS (gas chromatography-mass spectrometry) can be found in Hans-Joachim Hübschmann, Handbook of GC/MS: Fundamentals and Applications, Wiley-VCH, 2nd edition, 2008. Techniques for other methods as well as instrumentation for these methods are similarly known in the art.

A process optionally includes placing a second sample in a test chamber, optionally prior to exposing a first sample or a second sample to an environmental condition. A second sample is optionally exposed to the same environmental conditions, optionally for the same time periods as a first sample, or is exposed to differing environmental conditions. In some embodiments, a second sample is exposed to heat alone while a first sample is exposed to both heat and light. The inventors discovered that several materials or volatile types are emitted from various materials under differing conditions. These VOCs may react to form reaction products or may differentially collect on a substrate. Thus, a first sample and a second sample are optionally exposed to one or more environmental conditions simultaneously or sequentially. In some embodiments, a first sample is exposed to light and heat, while a second sample is exposed to heat alone.

To sequester a first or second sample from light, a sample is optionally placed behind a support (relative to the direction of light emission) where the support transmits less than 1% of light. In some embodiments, a support allows both samples to be exposed to heat, while sequestering one sample from light. Thus, a light exposure area and a light exclusion region can be created by the presence of a light blocking support.

While the term "support" is used, this is not limited to a surface that holds one or more samples in a position with the test chamber, although the support may do so. A support functions as a surface to form a light exposure area and a light exclusion region.

A process is performed for a test period. A test period is optionally formed of a singular set of environmental conditions that are constant or variable over the entire test period. A test period is optionally from 1 hour to 48 hours, optionally 24 hours. In some embodiments, a test period is 24 hours or less. Optionally, a test period does not exceed 24 hours. A test period optionally includes one or more test phases. A test phase is described herein as a first time, a second time or additional time. The environmental conditions during different test phases are optionally the same or different than other test phases. In some embodiments, a series of test phases are repeated until a test period is reached. Illustratively, a first time (illustratively, irradiation phase) is used, followed by heat only for a second time (illustratively, rest phase), and heat and light for a third time (illustratively, irradiation phase). This, or other set of phases in itself forms a test period, or the set of phases is repeated for an entire test period.

The processes provided are capable of detecting and optionally identifying one or more VOCs liberated from one or more samples with superior efficacy relative to prior methods used in the art.

Figure 2:
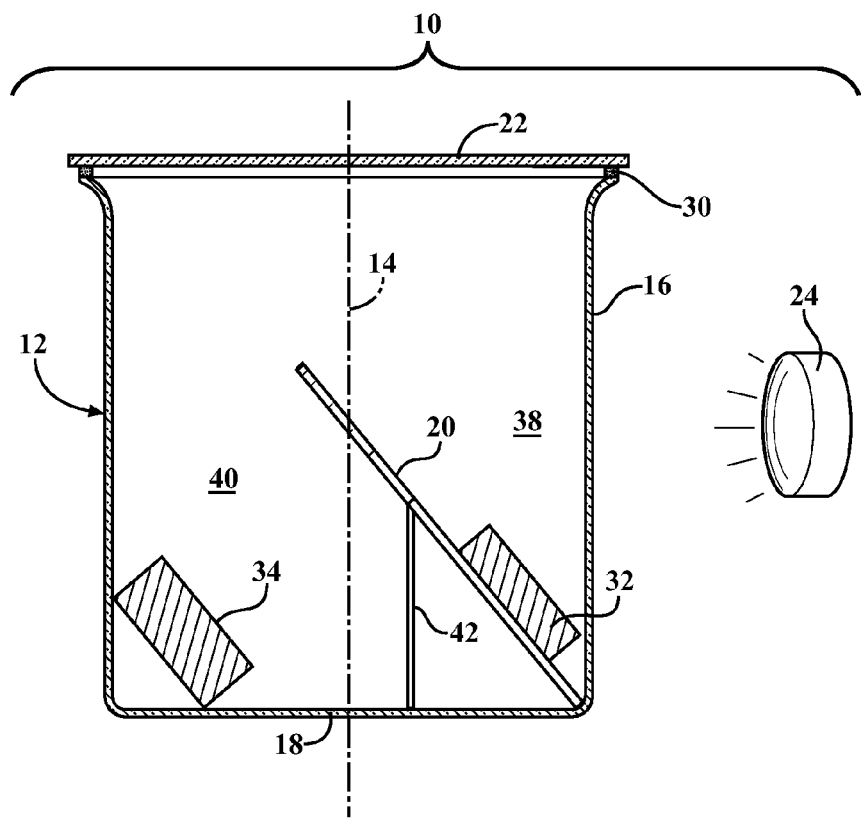
FIG. 2 illustrates one embodiment of a test chamber for use in an inventive process.

Also provided is an apparatus for producing and detecting one or more VOCs from one or more samples. An apparatus is suitable for performing a process of detecting a volatile organic compound from a sample as described herein. An apparatus includes a test chamber, a support, a substrate, and a light source. An illustrative example of an apparatus 10 is presented in FIG. 2. A test chamber 12 includes a vertical midline 14, a wall 16, and a floor area 18. A test chamber 12 is an enclosable chamber that allows for control of one or more environmental conditions within the test chamber 12. The test chamber 12 of FIG. 2 is depicted as having a substantially cylindrical outer shape such as that formed by a beaker. It is appreciated that other outer shapes are similarly operable. An outer shape is optionally regular or irregular. A test chamber 12 can have any outer shape including that of a cylinder. A test chamber 12 has a regular or irregular cross sectional area that is perpendicular to the vertical midline 14. A cross sectional area is illustratively circular, oval, square, rectangular, or any polygonal shape, or an irregular shape. The size of a cross sectional area is optionally uniform or variable along the direction of the vertical midline. Illustratively, a cross sectional area decreases partially or entirely in the vertical direction. An illustrative example of a vertically decreasing cross sectional area is a conical shape.

A test chamber 12 further includes a wall 16 with at least a portion that is transparent to light. A wall 16 optionally forms one side of a test chamber 12. A wall 16 is illustratively transparent to light of one or more wavelengths between 100 nm to 750 nm, or more. The term "transparent" as used herein is defined as capable of transmitting 50% or more of incident light of a particular wavelength. A wall or portion thereof is optionally formed of a material that is transparent to light of a desired wavelength or range of wavelengths. For example, UV-grade quartz (fused silica) glass shows greater than 80% transmission from approximately 180 nm to approximately 1500 nm. (See synthetic quartz glass available from Praezisions Glas & Optik GmbH, Germany.) Borosilicate glass shows typical transmission in excess of 50% from approximately 300 nm to approximately 2800 nm. (See BOROFLOAT glass available from Praezisions Glas & Optik GmbH, Germany.) Colorless acrylic material shows greater than 50% transmission of light of wavelength from approximately 290 nm through the visible spectrum. Other materials known in the art are similarly suitable for use in a wall 16. A wall or portion thereof is optionally formed of automotive glass. A wall 16 is optionally transparent across its surface area, or has a portion that is transparent such as a window. Illustratively, when a test chamber 12 is a cylinder, a wall is a portion of the cylinder that is transparent to light. A wall 16 is optionally any portion of a test chamber 12 that is transparent to light or has a portion thereof that is transparent to light.

A test chamber 12 and a wall 16 are optionally continuous or joined at a joint. A joint is optionally fixed or detachable. A wall 16 is optionally detachable or fixed to one or more other portions of a test chamber 12. In some embodiments, a wall is slideably connected to a test chamber. A wall 16 is optionally replaceable with one or more alternate materials such as those with differing, complementary, or contrasting transmission profiles. In some embodiments, a wall is a filter such as a bandpass filter or a cutoff filter.

Figure 3A:
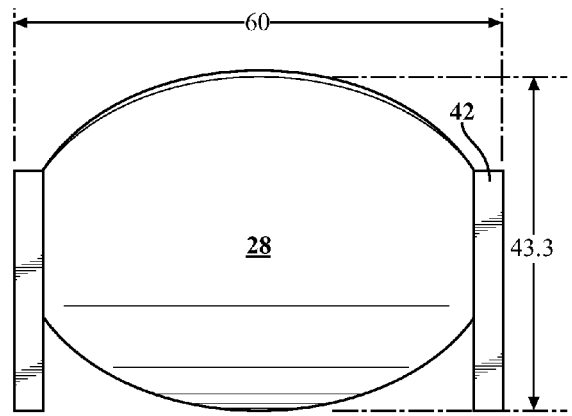
FIGS. 3A-3C illustrate one embodiment of a support.
Figure 3B:
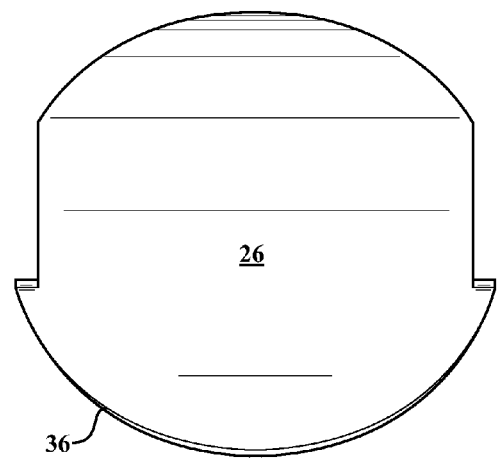
Figure 3C:
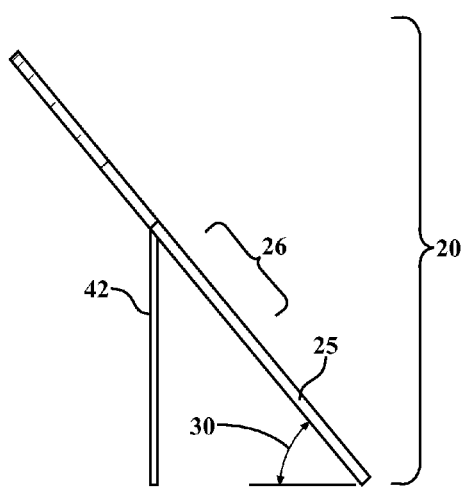

An apparatus 10 optionally includes a support 20 removably associated with the interior of a test chamber 12. A support 20 is capable of having a sample placed on a face of the support or otherwise supporting a sample in position to be exposable to light transmitted through the window 16. One embodiment of support 20 is illustrated in FIGS. 3A-3C. A support 20 includes a face 25 with a first side 26 and a second side 28. A first side 26 optionally is directed toward a wall 16 of a test chamber 12. A second side 28 is optionally directed away from a transparent wall or the direction of a light source. A face 25 is optionally placed at an angle 30 relative to the floor area 18. In some embodiments, an angle is from 5 to 90 degrees, or any value or range therebetween, in either direction relative to the floor area 18. Optionally, an angle is from 25 degrees to 60 degrees. Optionally, an angle is 45 degrees.

A face 25 optionally has an outer shape 36 that is complementary to the cross sectional area of the test chamber. Illustratively, the outer shape of the support is designed so as to fit against at least a portion of the wall(s) of the test chamber. The outer shape of the support illustrated in FIG. 3B is optionally such that the support fits within a cylindrical test chamber at an angle, optionally 45 degrees.

Also as shown in FIG. 3C, a support 20 optionally includes one or more arm members 42 that extend from the face toward the floor area of a test chamber when a support is positioned within a test chamber. An arm member 42 optionally serves to support a face at an angle relative to the floor area of the test chamber. Optionally, a support 20 includes one, two, three, four, or more arm members. Optionally, an arm member 42 is shaped so that light that is exposed to the light exposure area is not transmitted past the sides of a support into the light exclusion region.

A support is made of any material of suitable rigidity to hold a sample in position during a process of detecting a volatile organic compound. Illustrative materials include: glass; metals such as steel, aluminum, stainless steel, or other metals known in the art; polymeric materials such as acrylics, polyethylenes, polyurethanes, or other plastic material; other materials known in the art; or combinations thereof. In some embodiments, a support is made of a reflective material such that energy from light transmitted through a window or a wall of the test chamber does not cause a substantial increase in the temperature to which a sample resting against a support is exposed.

One embodiment of a support within a test chamber is depicted in FIG. 2. A support optionally includes a face 25 with a first side 26 oriented such that the support forms a light exposure area 38 when placed into a test chamber. A light exposure area 38 is a portion of the interior of a test chamber 12 that is exposable to light that is transmitted through a wall 16 of the test chamber 12. On the opposite side of the face 25 is a second side 28 oriented such that when a support is placed into a test chamber a light exclusion region 40 is formed on the second side of the support. A light exclusion region 40 is an area that is not exposable to direct light transmitted through a wall 16 of a test chamber 12. In some embodiments, a light exposure area 38 and a light exclusion region 40 are both exposable to environmental conditions other than light within the test chamber. Illustratively, both the light exposure area 38 and the light exclusion region 40 are exposable to the same temperature, humidity, or other environmental condition.

An apparatus for detecting volatiles from a sample also includes a substrate 22 that is moveably or removably associated with the test chamber 12, optionally at a position above a midpoint of the test chamber 12. A substrate 22 optionally acts as a removable cover that allows access to the interior of a test chamber for placement of one or more samples within the test chamber and also may act as a surface for the collection and subsequent detection of one or more VOCs. A substrate 22 includes a surface that is directed towards the interior of the test chamber. A surface of a substrate is optionally planar, curvilinear, or other shape suitable for the collection of one or more volatile organic compounds onto the substrate. The surface of a substrate is optionally smooth or textured. The substrate material is formed of any material suitable for the collection of one or more volatile organic compounds collected thereon. Illustrative examples include: glass such as automotive glass, silica glass, or other glass; plastics; metals; other material known in the art; or combinations thereof. In some embodiments, a substrate is formed of glass such as a borosilicate glass or other glass type known in the art. Optionally, automotive glass is used as a substrate. A substrate is suitably dimensioned to cover a portion of or the entire upper surface of a test chamber.

A substrate is removably, hingedly, or fixedly associated with a test chamber either via direct contact with one or more walls of the test chamber or by contact with an intermediate structure 30. An intermediate structure 30 optionally serves as a gasket between a substrate 22 and the interior of a test chamber 12 such that VOCs liberated within the test chamber are not free to escape the interior portion of the chamber, as well as isolates the interior of the test chamber such that particular environmental conditions can be created or maintained. An intermediate structure 30, such as a gasket, is made of any suitable material so that a seal can be formed between the substrate 22 and the wall 16 of a test chamber. Such materials illustratively include silicones, rubbers, cork, various other polymeric materials, adhesives, or other suitable material known in the art.

A substrate 22 is optionally coated, or otherwise contacted with one or more reflective materials. A reflective material is optionally layered upon, coated upon, or otherwise associated with a side of a substrate that faces away from the interior of a chamber. A reflective material provides a reflective surface for measurements of gloss or other reflective or clarity property of the substrate before, during or after a test procedure. A reflective material is optionally tin, aluminum, stainless steel, gold, silver, others known in the art, or combinations thereof.

An apparatus 10 also includes a light source 24 in optical contact with a light exposure area within a test chamber. A light source 24 is positioned to transmit light to the interior of the test chamber 12. A light source 24 is optionally located within the interior portion of a test chamber 12, or outside a test chamber 12 such that light emitted from the light source 24 is capable of being transmitted through a wall 16 of the test chamber into the interior portions to expose a sample in a light exposure area 38 to light emitted from the light source 24. A light source 24 is optionally a monochromatic light source or a broad spectrum light source. Illustrative examples of a light source include a laser or other monochromatic light source, a xenon arc lamp, a sulfur plasma lamp, another source of broad spectrum light such as white light optionally including or excluding ultraviolet light, other desirable light source, or combinations thereof. A light source is capable of emitting light of a wavelength and intensity as described herein.

One or more filters are optionally located in between a light source and a light exposure area. A filter is optionally associated with a wall of a chamber or with a light source. Filters are illustratively band pass filters that prevent light above or below a certain wavelength from being transmitted through the filter, or a cutoff filter. Such filters are known in the art and readily available from commercial sources. In some embodiments, a filter allows light to be transmitted into a light exposure area that is below a certain wavelength. Optionally, a filter transmits only ultraviolet light such as light with a wavelength of 400 nanometers or less. In some embodiments, a filter is capable of transmitting light with a specified wavelength or wavelength range so as to be useful in a process as described herein.

An apparatus is of suitable structure or dimensions so that it can be used to expose one or more samples to one or more environmental conditions within the interior of a test chamber for a test period. As an illustrative example of one embodiment of a test chamber, a Griffin-type 250 ml beaker is used. A Griffin-type beaker optionally has a height of 86 mm and a diameter of 67 mm. An outer surface forms a wall through which light may pass to expose a sample in a light exposure area. Other sizes, shapes, dimensions, etc. of a test chamber are also operable.

Various aspects of the present invention are illustrated by the following non-limiting examples. The examples are for illustrative purposes and are not a limitation on any practice of the present invention. It will be understood that variations and modifications can be made without departing from the spirit and scope of the invention. Reagents illustrated herein are commonly commercially available, and a person of ordinary skill in the art readily understands where such reagents may be obtained.

Example 1

Detection of Volatile Organic Compounds

Figure 4A:
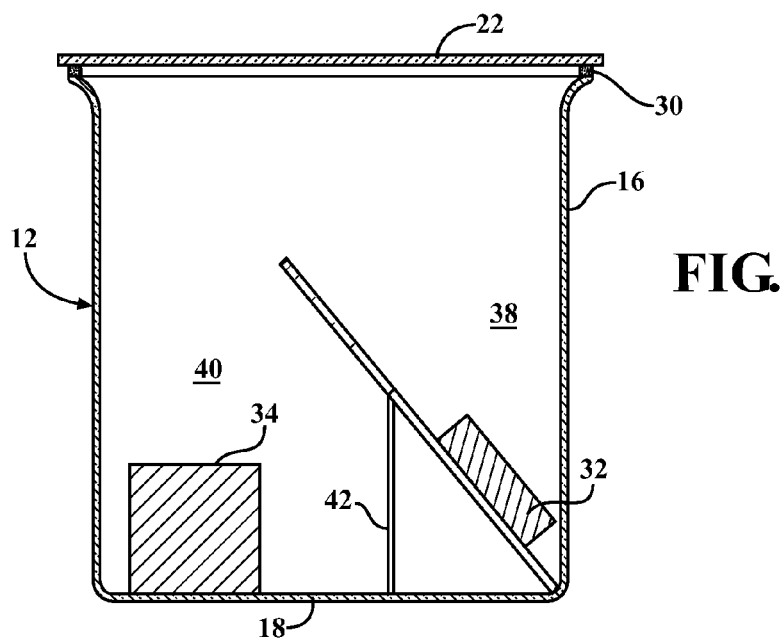
FIGS. 4A-4B illustrate one embodiment of a test chamber and assembly for placing a test chamber in a weatherometer or other system, respectively, for producing an environmental condition.

A cylindrical test chamber substantially as depicted in FIG. 4A is assembled of a soda-lime glass with a height of 86 mm and a diameter of 73.5 millimeters is obtained from Quartz Scientific, Inc., Fairport Harbor, Ohio. The upper surface of the test chamber is ground flat (no pour spout). A sample holder (support) made from stainless steel, and sized to fit against the inner surface of a portion of the test chamber, is placed into the interior of the test chamber to form a light exposure area and a light exclusion region. The support covers approximately 60% of the floor area such that volatiles from a sample in the light exclusion region and light exposure area are capable of accessing a substrate.

A sample 32 of adhesive formed of chlorinated polymers and petroleum resins (370U; Sunstar Engineering Americas, Inc.; Springboro, Ohio) is placed into the test chamber in the light exposure area 38 resting against the support. A second sample 34 of polyether based urethane polymer foam (Flexible Urethane Foam; Flexible Foam Products, Inc., Elkhart, Ind.) is placed in the light exclusion region 40.

Figure 4B:
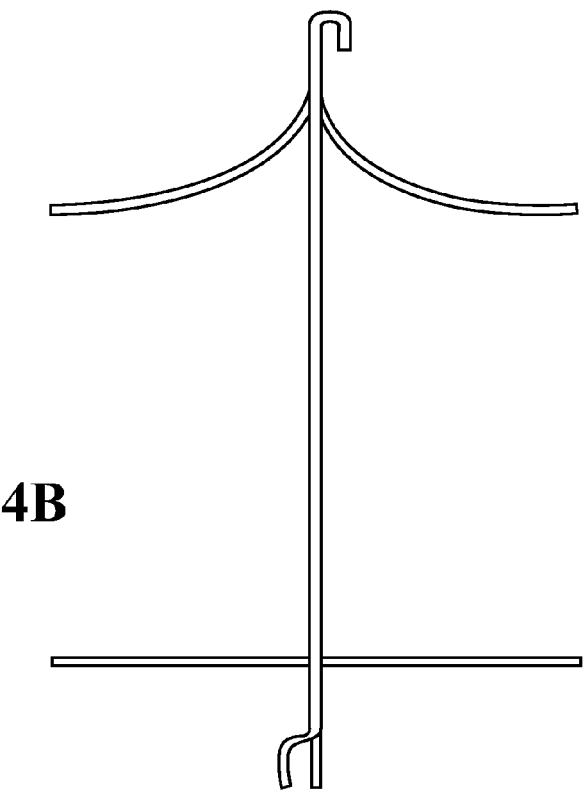

A substrate 22 made of borosilicate glass (84 mm×100 mm) is pre-weighed and affixed to the upper surface of the test chamber by an intermediate silicone seal with 80 mm O.D., 67 mm I.D., and a thickness of 0.06 inches. The substrate 22 is coated with tin on the surface opposite the interior of the test chamber. The enclosed test chamber is placed in a holder assembly depicted in FIG. 4B. The test chamber is then placed into a weatherometer equipped with a water cooled xenon 7.0 kW lamp with an irradiance of 150 W/m$^2$ (300-400 nm) (Suga model SC-700FT from Suga Test Instruments Co., Ltd.) for a test period.

The samples are exposed to a series of exposure phases for a 24 hour total test period as in Table 1. Temperature is confirmed by an IR thermometer directed at each sample.

TABLE 1

| Exposure Phase Parameters | | | | |
|---|---|---|---|---|
| Exposure Phase | Time | Heat | Light | Humidity |
| First Exposure | 0.5 hours | 89° C. | On | 50% |
| Rest | 1 hour | 38° C. | Off | 95% |
| Second Exposure | 3 hours | 89° C. | On | 50% |

At the end of the test period, the substrate 22 is removed for analyses of the presence or absence of volatiles on the surface by several methods. Visual examination indicates a fogging on the surface of the substrate 22 indicating the presence of volatiles accumulating on the surface during the test period. The presence of one or more volatiles is confirmed by gravitometry. The substrate 22 is placed on a scale for determination of mass following the test period. An increase in mass is observed relative to prior to the test period indicating the presence of volatiles.

Example 2

Detection of Volatiles by Glossometry

The sample plate of Example 2 following a test period is subjected to glossometry using a RHOPOINT IQ (Goniophotometer) 20°/60°/85° from Rhopoint Instruments, East Sussex, UK, used as per the manufacturer's instructions. The gloss meter is used to take measurements before the test period. The same measurements are performed after the test period. The surface demonstrates a reduction in gloss profile indicating the presence of one or more VOCs on the surface of the substrate following the test period Example 3

Identification of Volatiles on a Substrate

Figure 5A:
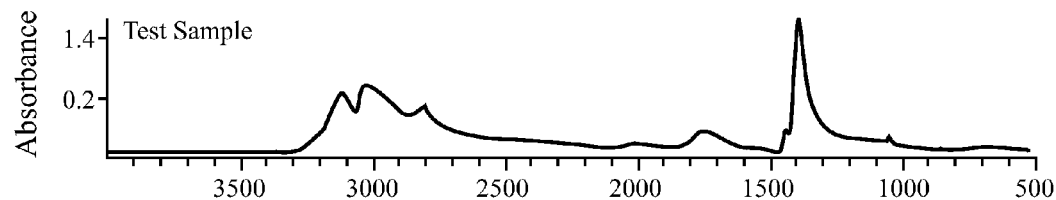
FIGS. 5A-5C illustrate FITR spectra of VOCs produced in a test chamber according to one embodiment of the inventive process that illustrates the detection of ammonium chloride and other volatiles emitted from exemplary samples during one embodiment of an inventive process.
Figure 5B:
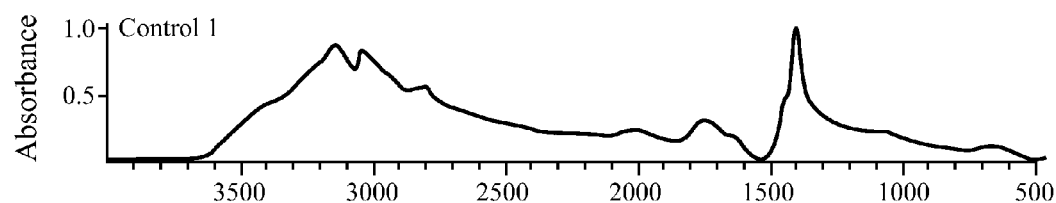
Figure 5C:
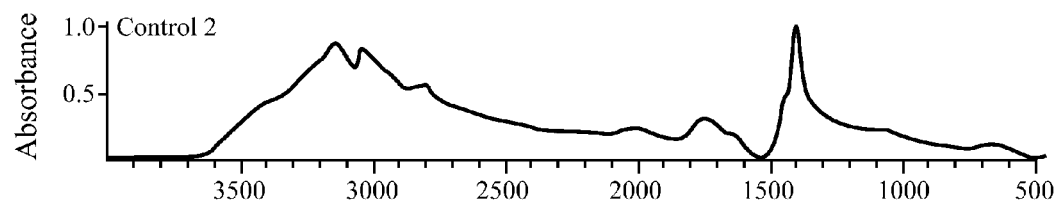

The identity of the volatiles collected on the surface of the substrate 22 of Example 1 is determined by FTIR. A section of residue from the substrate is scrapped into a clean sample jar using a razor blade. Sample is then fixed onto the FTIR diamond head and subjected to FTIR analyses using a MIR8025 Modular FT spectrometer available from Newport Corp., Irvine Calif. The FTIR instrument scans the material over the wavelength range of 4000 nm to 300 nm. The results generated using the OMNIA software of the scan are illustrated in FIG. 5. The OMNIA library is then scanned for matching samples. One VOC is identified as ammonium chloride.

The experiments of Example 1 are repeated with a single sample in the test chamber. A first test period is run with a sample 32 of the adhesive of Example 1 including exposure to the same light environmental conditions. A second test period is run with a clean test chamber and substrate with a sample 34 of the foam of Example 1 under no light conditions similar to the light exclusion region of Example 1. The results indicate that the ammonium chloride is a reaction product of the volatiles produced by the adhesive and the foam.

Various modifications of the present invention, in addition to those shown and described herein, will be apparent to those skilled in the art of the above description. Such modifications are also intended to fall within the scope of the appended claims.

It is appreciated that all reagents and materials are obtainable by sources known in the art unless otherwise specified.

Patents and publications mentioned in the specification are indicative of the levels of those skilled in the art to which the invention pertains. These patents and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process of detecting a volatile organic compound produced from a sample comprising:
    placing a first sample and a second sample is a test chamber, said second sample placed entirely behind a support relative to the direction of a light source, said support transmitting less than 1% of light emitted from said light source;
    exposing for a first time said first sample to light from said light source, said light having a wavelength less than 400 nanometers, said exposing within said test chamber;
    subjecting said first sample and said second sample to a temperature; and
    detecting the presence or absence of one or more reaction products produced from a reaction of one or more volatiles from said first sample and one or more volatiles from said second sample, said reaction product produced from the step of exposing and the step of subjecting.

2. The process of claim 1 further comprising collecting said one or more reaction products on a substrate.

3. The process of claim 1 wherein said light has a wavelength from 315 nanometers to 400 nanometers.

4. The process of claim 1 wherein said temperature is between 35 degrees Celsius and 85 degrees Celsius.

5. The process of claim 1 wherein the step of said exposing and the step of said subjecting are both performed during said first time.

6. The process of claim 1 further comprising the step of ceasing said exposing after said first time;
    incubating said first sample and said second sample for a rest time; and
    re-exposing said first sample to light with a wavelength less than 400 nanometers for a second time.

7. The process of claim 6 wherein the length of said second time is greater than the length of said first time.

8. The process of claim 6 wherein said rest time is 30 seconds or more.

9. The process of claim 1 further comprising placing said first sample in said test chamber prior to said step of exposing.

10. The process of claim 1 further comprising the step of subjecting said second sample to a temperature at or in excess of 25 degrees Celsius.

11. The process of claim 1, wherein said volatiles are detected by FTIR.

* * * * *